United States Patent [19]
Cody et al.

[11] Patent Number: 5,675,071
[45] Date of Patent: Oct. 7, 1997

[54] PASSIVE ACOUSTICS PROCESS TO MONITOR TRANSFER LINES OF A REACTOR

[75] Inventors: George D. Cody, Princeton, N.J.; Eugene R. Elzinga, Jr., Marquette, Mich.; Charles L. Baker, Jr., Thornton, Pa.

[73] Assignee: Exxon Research & Engineering Company, Florham Park, N.J.

[21] Appl. No.: 577,696

[22] Filed: Dec. 22, 1995

[51] Int. Cl.⁶ .................. G01N 9/00; G01F 1/20
[52] U.S. Cl. .............. 73/32 A; 73/19.03; 73/861.18
[58] Field of Search .................. 73/32 A, 19.03, 73/19.04, 28.01, 861.04, 861.18, 861.19, 861.72, 861.73, 290 V

[56] References Cited

U.S. PATENT DOCUMENTS

| | | |
|---|---|---|
| 3,012,848 | 12/1961 | Levey, Jr. et al. |
| 4,320,665 | 3/1982 | Cain ................... 73/861.04 |
| 4,357,603 | 11/1982 | Roach et al. ........... 73/81.21 |
| 4,993,264 | 2/1991 | Cody et al. ............. 73/579 |
| 5,022,266 | 6/1991 | Cody et al. ............. 73/579 |
| 5,207,090 | 5/1993 | Downing, Jr. ........... 73/61.75 |
| 5,207,107 | 5/1993 | Wolf et al. ............. 73/861.04 |
| 5,526,696 | 6/1996 | Cappi ................... 73/861.04 |

Primary Examiner—Michael Brock
Assistant Examiner—Helen C. Kwok
Attorney, Agent, or Firm—Ronald D. Hantman

[57] ABSTRACT

The present invention is a method for the non-intrusive determination of average particle velocity and average particle mass density from the mass flux and RMS acceleration in a gas/particle transfer line. The method includes the steps of determining the RMS acceleration of the wall of the transfer line at one or more positions along the length of the transfer line, determining the average mass flux through the transfer line, and from both quantities determining the average particle mass density or the average particle velocity from the RMS acceleration and the average mass flux.

7 Claims, 11 Drawing Sheets

PASSIVE ACOUSTICS PROCESS TO MONITOR TRANSFER LINES OF A REACTOR

BACKGROUND OF THE INVENTION

The present invention relates to a passive acoustics process to monitor transfer lines of a reactor.

Fluidized beds, and the associated transfer lines that supply particle/gas streams to and from them, play a significant role in a variety of petroleum refining, chemical, drying and combustion processes. A recent article in Science [A.M. Squires, M. Kwauk and A. A. Avidan, Science 230, 1329–1136 (1985)] reviewed the use of fluidized bed reactors for combustion of powdered coal as well as other applications such as "roasting ores, calcining carbonates calcining or burning wastes, drying solids, cracking hydrocarbons, and converting gasses catalytically". *Fluidization Engineering*(Daizo Kunii and Octave Levenspiel, Krieger, Malabar, Fla. 1987) also reviews a variety of physical, synthetic, and refining operations that are based on fluidization of gas/particle systems.

Transfer of the solids/gas stream into, and in some cases out of fluidized bed reactors, is accomplished through transfer lines or large diameter pipes where particles are transported in a high velocity gas stream. These transfer lines are sometimes designated "standpipes" when they remove a gas stream of particles from a fluidized beds, or "risers" when they supply a gas stream of particles to a fluidized bed. The density of particles in transfer lines is somewhat less than that in fluidized beds and for common transfer lines range from 1 to 30% of the density of water.

The local mass density in a section of the transfer line, $\rho_m$, the local particle velocity, $V_p$, and the local cross-sectional area of the pipe of internal diameter D, define the local mass flux of particles through the transfer line, F[kg. m$^2$sec] through a spatial average across the cross-section of the pipe:

$$F = \langle \rho_m V_p \rangle, \qquad (1)$$

The mass flow rate [kg/sec] is then given by $F(\pi D^2/4)$. In many cases of interest the slip velocity, the difference between the particle velocity and the gas velocity, is small and constant across the cross-section and a considerably simpler approximation to Eq. (1) can be made. The spatial average of the product of the particle density and particle velocity given by Eq. (1) is replaced by the product of the average particle density ($\rho_a = \langle \rho_m \rangle$) and average particle velocity ($V_a = \langle V_p \rangle$) as shown in Eq. (2).

$$F = \langle \rho_m V_p \rangle \cong \langle \rho_m \rangle \langle V_p \rangle = \rho_a V_a \qquad (2)$$

Where the simplification represented by Eq. (2) is valid, individual measurements of any two of the three quantities, F, $\rho_a$, and $V_a$, are sufficient to determine the third.

Fluidized beds, and the transfer lines that supply and extract particles to and from them, are designed to operate continuously for times as long as several years. Numerous factors can interfere with the intended long-term operation of the transfer line. Undetected design failures can lead to excessive particle velocities in regions of the transfer line which erode critical components that maintain particle flow such as gas or feed injectors and even the refractory wall of the transfer line. High particle velocities also lead to particle attrition and excessive generation of "fines" which can then be lost in the gas streams that exit the fluidized bed.

Attempts to change operating conditions to accommodate higher or lower particle mass flow rates, as frequently occurs in cat-cracking with changing "feed rates", can lead to undetected instabilities within the transfer line. One example of such instabilities are stagnant "bubbles" that limit the flow of particles through the line. Regions of high particle densities ("slugs") can also exert damaging forces on structural supports and components. In general, critical components controlling the flow of particles and gasses can fail for a multitude of reasons. If their failure remains undetected, performance of the transfer line gradually deteriorates.

Borzone, et al. [L. A. Borzone, G. E. Klinzing and W. C. Yang, *Powder Technology*, 62.277–290 (1990)] review some of the problems associated with coal combustion and gasification units. These authors note that "the pneumatic conveying of solids at high temperatures is an operation of growing importance in the area of coal technology. Coal combustion and gasification units must handle solid-loaded streams at high temperatures, close to slagging conditions. Under these conditions, erosion and corrosion become major problems, affecting the continuous operations of such systems".

In order to operate fluidized bed processes efficiently, there is thus a critical need to monitor the operating performance of the transfer lines that permit them to operate continuously. Quantitative information of the operating state of a transfer line in terms of the variables F, $V_a$ and $\rho_a$ can: (1) Assist the process operator and engineers in identifying the source of operating limitations on changes in particle mass flow rate, (2) Assist the process operator and engineers in identifying and correcting flow conditions that may lead to wall erosion or damage of components; (3) Assist the operator in identifying and correcting flow conditions that lead to excessive particle attrition and hence particle loss; (4) Assist the process operator and engineers in start-up and shutdown of the process; and (5) Assist process design engineers in validating semi-emperical models for particle flow as well as identifying flaws in design.

The novel discoveries of the present invention include the observations that:

1. Random particle impact on the inside wall of a transfer line dominates other sources of wall vibrational noise in certain frequency ranges in commercial transfer lines.

2. Composite refractory/steel walls of transfer lines can exhibit localized wall resonances that respond to particle impact within a lateral region of the order of 1—3× the thickness of the wall. If this is not the case, selective damping of the wall of the transfer line can localize the response of the accelerometer to a similar radius of sensitivity.

3. Selective processing of the power spectrum of the output of the accelerometer can supply quantitative information about the local particle density and local particle velocity within the transfer line as well as on changes that occur in any of these quantities.

SUMMARY OF THE INVENTION

The present invention is a method for the non-intrusive determination of average particle velocity and average particle mass density from the mass flux and RMS acceleration in a gas/particle transfer line. The method includes the steps of determining the RMS acceleration of the wall of said transfer line at one or more positions along the length of said transfer line, determining the average mass flux through the transfer line, and from both quantities determining the average particle mass density or the average particle velocity from the RMS acceleration and the average mass flux.

DESCRIPTION OF THE PREFERRED EMBODIMENT

The present invention is a process for the non-intrusive measurement and monitoring of the local flow parameters (mass flux, F; average particle velocity, $V_a$; average particle density, $\rho_a$) of the contained two phase (particle/gas) fluid in a transfer line and using this information to obtain local information of the flow state of the particle flow within the transfer line. More specifically, it describes a non-intrusive measurement that utilizes an accelerometer or series of accelerometers mounted appropriately on the external wall of the transfer line, whose output is signal processed as described herein to:

(1) Estimate and monitor average particle velocity and mass density across a cross section of a transfer line if the mass flow rate in the line is known.

(2) Detect changes in average particle velocity and mass density across a cross section of a transfer line due to changes in the operating condition of components if the mass flow rate in the line is known.

(3) Measure and monitor average mass flow rate in the line based on a one-time empirical calibration of the line and measurement location in question.

(4) Detect changes in average mass flow rate across a cross section of a transfer line due to changes in the operating condition of components in the line if the gas flow in the line is constant.

(5) Identify regions of the transfer line with high gas velocity which could contribute to the generation of an excessive number of catalyst fines and monitor the performance of modifications of gas flow to eliminate high particle velocities which cause wall erosion. As noted high particle velocities also lead to particle erosion and excessive loss of catalysts as well as excessive generation of fines.

(6) Identify regions of the transfer line with "stagnant bubbles" which limit increases in particle mass flow in the line.

(7) Validate changes in operating conditions and line design to eliminate by appropriate design or operating changes localized regions of the transfer line with "stagnant bubbles" which limit increases in particle mass flow in the line.

MATHEMATICAL BACKGROUND

The power spectrum of the acceleration of a wall of a transfer line can be obtained by attaching an accelerometer to the wall and analyzing the random time signal of the wall acceleration by standard signal processing techniques either in real time or for recorded data. The output of such signal processing techniques which are well known to those skilled in the art is the power spectrum, $S_A(f)$, of the wall. The Root Mean Square Acceleration (RMS Acceleration), A, over the band of frequencies between $f_1$ and $f_2$ is defined through the integral of the power spectrum as $$A^2 = \int_{f_1}^{f_2} S_A(f) df \qquad (3)$$

For many applications the quantity A can be obtained by simple band-pass filtering of the acceleration time signal over a suitable band $(f_1 \to f_2)$ of frequencies about a central frequency, $f_o$, where $f_1 = f_o - B$ and $f_2 = f_o + B$, and the total bandwidth=2B followed by measurement of the power within that band width. In the following we continue to use the concept of the acceleration Power Spectrum, although those skilled in the art will recognize that there are other, and sometimes more convenient, techniques for obtaining RMS Acceleration over a given frequency band as noted above.

The power spectrum of the acceleration, $S_A(f)$, can be shown by the theory of random signals applied to structure borne sound of a wall to be given by the product of the magnitude of the transfer function of the wall, $|H(f,r_i)|^2$ and the power spectrum of the random force at location $r_i$ exciting the wall, $S_F(f,r_i)$.

$$S_A(f) = \Sigma |H(f,r_i)|^2 S_F(f,r_i) \qquad (4)$$

The transfer function of the wall can be empirically obtained from the average response of the accelerometer on the wall to the time dependent force on the wall from an impact hammer a distance "$r_i$" away from the accelerometer (for example a Bruel and Kjaer Impact Hammer 9202). As is known to those skilled in the art of structure borne sound, the quantity $H(f,r_i)$ is defined as $$H(f,r_i) = \left( \frac{a(f,0)}{F(f,r_i)} \right),$$

where a (f,O) and $F(f,r_i)$ are the respective Fourier Transforms of the accelerometer and hammer pulse, and the bracket, <>, denotes an average over hammer excitations.

For composite refractory walls of transfer lines found in petroleum refineries $|H(f,r_i)|$ is often well approximated by a localized response $$|H(f,r_i)| = H_o \left| \frac{w^2}{(f-f_o)^2 + w^2} \right|^{1/2} e^{-(\frac{r_i}{R_o})} \qquad (5)$$

Eq. (5) contains four constants $R_o$, $f_o$, w and $H_o$ all of which can be obtained accurately by calibration or estimated by calculation:

(1) The constant, $R_o$, defines a circle of response about the accelerometer. For many composite steel/refractory walls found in petroleum, refining, $R_o$ is of the order of the 1 to 3× the wall thickness.

(2) The constants, $f_o$ and w, are the frequency and width of the wall resonance that is commonly exhibited in the composite steel/refractory walls found in petroleum refining. It has been found that $f_o$ is well approximated by the classical formula for the one-dimensional resonance of the composite wall.

(3) The constant, $H_o$, is the acceleration response of the wall at the point of impact and at the frequency $f_o$. Those skilled in the art of structure borne sound will recognize that this quantity can be readily estimated from the geometry and elastic properties of the wall [R. H. Lyon, *Statistical Energy Analysis of Dynamical Systems: Theory and Applications* (MIT Press, Cambridge, Mass. 1975), see also L. Cremer and M. Heckl, *Structure Borne Sound* (Springer-Verlag, Berlin (1988)]. Those skilled in the art of structure borne sound also know that the quantity $|H(f,R)|$ (and $H_o$) can be measured directly by impact hammer exciation of the wall of the transfer line. Thus all the constants of Eq. (5) can be obtained accurately by calibration or estimated by calculation.

For random elastic impact of particles of mass $M_p$ and normal velocity $V_n$ with a rigid wall, it can be shown that the momentum exchange with a ring shaped area element of the wall at a distance "$r_i$" from the accelerometer, can be described by a power spectrum given.

$$S_p(f,r_i) = (2M_p(r_i)V_n(r_i))^2 \rho_b(r_i) V_n(r_i) 2\pi r_i dr_i \qquad (6)$$

where $\rho_b(r_i)$ is the volume density of particles adjacent to the element of area $2\pi r_i$ $dr_i$ and $V_n(r_i)$ is the normal velocity of particles to the wall. In what follows we will drop the explicit dependence of the quantities, $M_p$, $V_n$, $\rho_b$ on distance $r_i$.

The absence of any explicit dependence on frequency on the fight hand side of Eq. (6) requires some discussion. It depends on two considerations: (1) shortness of the particle impact time and an upper limit to the frequency where accelerometers can be utilized. This upper limit must be below their intrinsic or mounting resonance and is hence of the order of 30 kHz. The particle impact time in turn determines the maximum frequency below which the power spectrum $S_p(F,r_i)$ is independent of frequency. This frequency, $f_p$ is approximately given by the velocity of sound in the particle divided by 10 times the particle diameter. Thus the frequency independence of Eq. (6) is be valid for particles with diameters as large as a few millimeters for an upper limit in frequency of 40 kHz.

From Eqs. (4) to (6), replacing the summation by an integeral $$A^2 = G_o(4M_p\rho_m V_n^3) \qquad (7)$$

where $\rho_m$ is the average mass density of the fluid gas mixture, $M_p$ the average particle mass and $V_n$ the average particle velocity normal to the wall of the transfer line. We can define $M_p$ in terms of an average particle diameter, $d_p$ and an average particle density $\rho_p$; thus $M_p = (\pi/6)\rho_p d_p^3$. The quantity $G_o$ is a property of the wall alone and is given by $$G_o = \int_{f_1}^{f_2} |H(f)|^2 df \qquad (8)$$

where $|H(f)|^2$ defines the spatial integral of the transfer function $$|H(f)|^2 = \int_o^\infty |H(f,r)|^2 2\pi dr. \qquad (9)$$

For the form of the transfer function exhibited in Eq. (5) and where $f_2 \gg f_o \gg f_1$ $$G_o = [H_o^2 w\pi][(\pi/2)R_o^2] \qquad (10)$$

For walls of transfer lines that do not exhibit the localized resonance defined by Eq. (5), those skilled in the art of classical structure borne sound will realize that there is an equivalent form for the quantity $G_o$ that depends only on the acoustic properties of the wall and the frequency band $f_1$ to $f_2$. For smooth walls where the range is over a band of width 2B centered on the frequency $f_o$, this equivalent form can be written as:

$$G_1 = (|H(f_o,0)|^2)(4B\eta_s)(R_1^2) \qquad (11)$$

where $$|H(f_o,0)| = \left( \frac{\pi\sqrt{3} f_o}{2h^2 \rho C_e} \right) \qquad (12)$$

The constants in Eq. (12) refer to a wall constructed of a rigid material of thickness h, density $\rho$, and extensional sound velocity $C_e$. The quantity $\eta_s$ is a dimensionless damping constant for the wall and $R_1$ a damping distance defined by $$R_1^2 = \left( \frac{hC_e}{\pi f_o \eta_s^2} \right) \qquad (13)$$

The existence of localized resonances in the composite wall of the transfer line is helpful in identifying the source of the wall excitation but is not critical to the local measurement feature of the patent, which can also be obtained by applying an annular ring of damping material around the accelerometer.

Eqs. (11–12) are well known to those skilled in the art of structure borne sound [R. H. Lyon, *Statistical Energy Analysis of Dynamical Systems: Theory and Applications* (MIT Press, Cambridge, Mass. 1975), see also L. Cremer and M. Heckl, *Structure Borne Sound* (Springer-Verlag, Berlin (1988)]. Thus for a wall that does not exhibit localized resonances, the general form of Eq. (7) coupling the RMS accleration of the wall, A, to the properties of the fluidized gas/particle system confined by the wall is maintained. Based on a suitable choice of central frquency, $f_o$, and bandwidth, 2B, chosen so that particle noise dominates the accleration power spectrum, the RMS acceleration is again given by an equation of the form of Eq. (7):

$$A^2 = G_1(4M_p\rho_m V_n^3) \qquad (14)$$

and in general, $$A^2 = (4M_p G)(\rho_m V_n^3) \qquad (15)$$

where G represents either $G_o$ or $G_1$.

Important to the application described in this patent is the separation of Eq. (14) into a part that depends on the properties of the wall (G) and a part that depends on the properties of the two phase fluid (particle/gas) on the interior of the wall, $(4M_p \rho_m V_n^3)$. Thus changes in the quantity A will respond to changes in the quantities, $V_n$ and $\rho_m$ from reference or base case conditions. Furthermore one time calibration of the accelerometer through impact hammer excitation to determine the quantity $|H(f_o,r_i)|$ is sufficient to determine the magnitude of G.

Eq. (14) has been derived from the impact of solid particles within the two phase medium as the equivalent of a random impact of many hammers. It is the vibrational equivalent to the electrical phenomena of "shot noise". Eq. (14) relates an easily measured quantity, A, to properties of the particles adjacent to the wall. Thus A, can be used to monitor the flow state in terms of changes in the quantity $\rho_m$, $M_p$, and $V_n$. Large changes in $M_p$ are unexpected for many petrochemical processes and a major use of the invention is to monitor $\rho_m$ and $V_n$.

Combining Eq. (14) with Eq. (2), $F=V_a\rho_a$, identifying $\rho_m$ with $\rho_a$, and scaling the velocities with respect to the gas superficial velocity, $V_s$, yields the equations for $V_a$ and $\rho_a$.

$$V_a=(R/S)^{3/2}(4M_pG)^{-1/2}(F)^{-1/2}(A) \quad (16)$$

$$\rho_a=(S/R)^{3/2}(4M_pG)^{1/2}(F)^{3/2}(A)^{-1} \quad (17)$$

where $$S=V_s/V_a \quad (18)$$

$$R=V_s/V_a$$

These are the fundamental formulas underlying this invention.

The parameter G is determined from the relationship $$(4M_pG_o)^{1/2}=((\pi^2/2)H_o^2R_o^2w(4\pi/6)\rho_p d_p)^{1/2} \quad (19)$$

in the case of $G_o$, or by combining Equations (11),(12), and (13) when $G_1$ must be used.

Because $M_p$ and G are, respectively, parameters of the transported particles themselves and the transfer line alone, the relationship $$(4M_pG)^{1/2}=K[m^2/kgsec] \quad (20)$$

holds in general. K is a characteristic parameter of the system that does not change over time. K can be determined by direct measurement of the average particle mass, and the mechanical and elastic properties of the transfer line. K can also be determined by a one time calibration described below.

It has been discovered for a wide variety of transfer lines carrying particles ranging from 60 to 150 microns in diameter under known flow conditions that a reasonable approximation $S \cong R \cong 0.7$. Under these circumstances Eq. (15) can be written (note [] indicates units)

$$Va[m/s] = K\left(\frac{A[M^2/s]}{F[Kg/m^2sec]^{1/2}}\right) = \frac{KA}{F^{1/2}} \quad (21)$$

and Eq. (16) can be written $$Pa[Kg/m^3] = \frac{F[Kg/m^2sec]^{3/2}}{KA[M^2/s]} = \frac{F^{3/2}}{KA} \quad (22)$$

K can be measured as shown above. Additionally, if F, A, and one of $V_a$ or $\rho_a$ are known, then K may be empirically determined.

The average particle velocity, $V_a$, for constant flux, F, is proportional to the RMS acceleration, A, and the average mass density, $\rho_a$, of the particles in inversely proportional to the RMS acceleration, A, with the same assumptions. The simplicity of this result is surprising and facilitates one time calibration of Eq. (21) and Eq. (22) when any two of the following three quantities are known in a transfer line: (1) average particle velocity $V_a$; (2) average mass density $\rho_a$; (3) average mass flux, F.

Therefore, values of $\rho_a$ and $V_a$ can be obtained in these cases where K is known simply by measuring flux (F) and the mean square acceleration A. The calculation of $\rho_a$ does not require calculation of $V_a$ and vice versa.

Steady state flow through the transfer lines is determined by equilibrium temperature measurements and slide valve settings. Measurement of the average mass flux, F, which is usually determined by global process conditions such as heat balance or from system pressure drops, makes it possible using Eq. 21 and 22 to determine the average particle density, $\rho_a$, and average particle velocity, $V_a$ at a specific locations from a non-intrusive, passive measurement of the RMS Acceleration at the point in question.

We note from Eq. (16–22) that a measurement of the RMS acceleration, A, over a frequency band in which particle impact noise dominates other sources of noise is sufficient to:

(1) Determine the average particle velocity, $V_a$ and the average particle density $\rho_a$, if the mass flux through the line is known, and the value of K is known either by calibration or measurement.

(2) Identify regions of the transfer line where the average particle velocity is high enough to cause erosion of a refractory wall at constant flow rate. As noted high particle velocities also lead to particle attrition and excessive loss of particles as well as excessive generation of fines into the atmosphere.

(3) Identify regions of the transfer line where "stagnant bubbles" limit increased in flow.

(4) Determine by the temporal variation in the RMS acceleration A if "slugging" is occurring.

(5) Validate design values for average particle velocity and mass density for a given flow mass flow rate.

In all of the above cases measurements of the quantity A can either be made on demand with portable equipment or in real time with permanently mounted accelerometers suitable local signal processing and transmission of appropriate signals to a control room.

A feature of the invention is the ability to place an accelerometer on the steel shell of a refractory lined vessel or pipe and obtain the RMS acceleration in a frequency band where particle impact noise dominates the acceleration power spectrum. Since in most refining or chemical processes the mass flux carded by the transfer line is known, the required information on the quantity F is not a limitation on the usefulness of the method described by this patent.

Critical to the application is the frequency independence the force power spectrum of particle impact. As noted earlier this limitation restricts the application to particles less than few millimeters for frequencies below 40 kHz.

Direct determination of the constant G can be made by impact hammer measurements on the external wall of the transfer line, although calculation through the usual equations of structure borne sound may be sufficient.

The existence of localized resonances in the composite wall of the transfer line is helpful in identifying the source of the wall excitation but is not critical to the local measurement feature of the patent which can also be obtained by applying an annular ring of damping material around the accelerometer.

IMPLEMENTATION OF THE INVENTION

Figure 1:
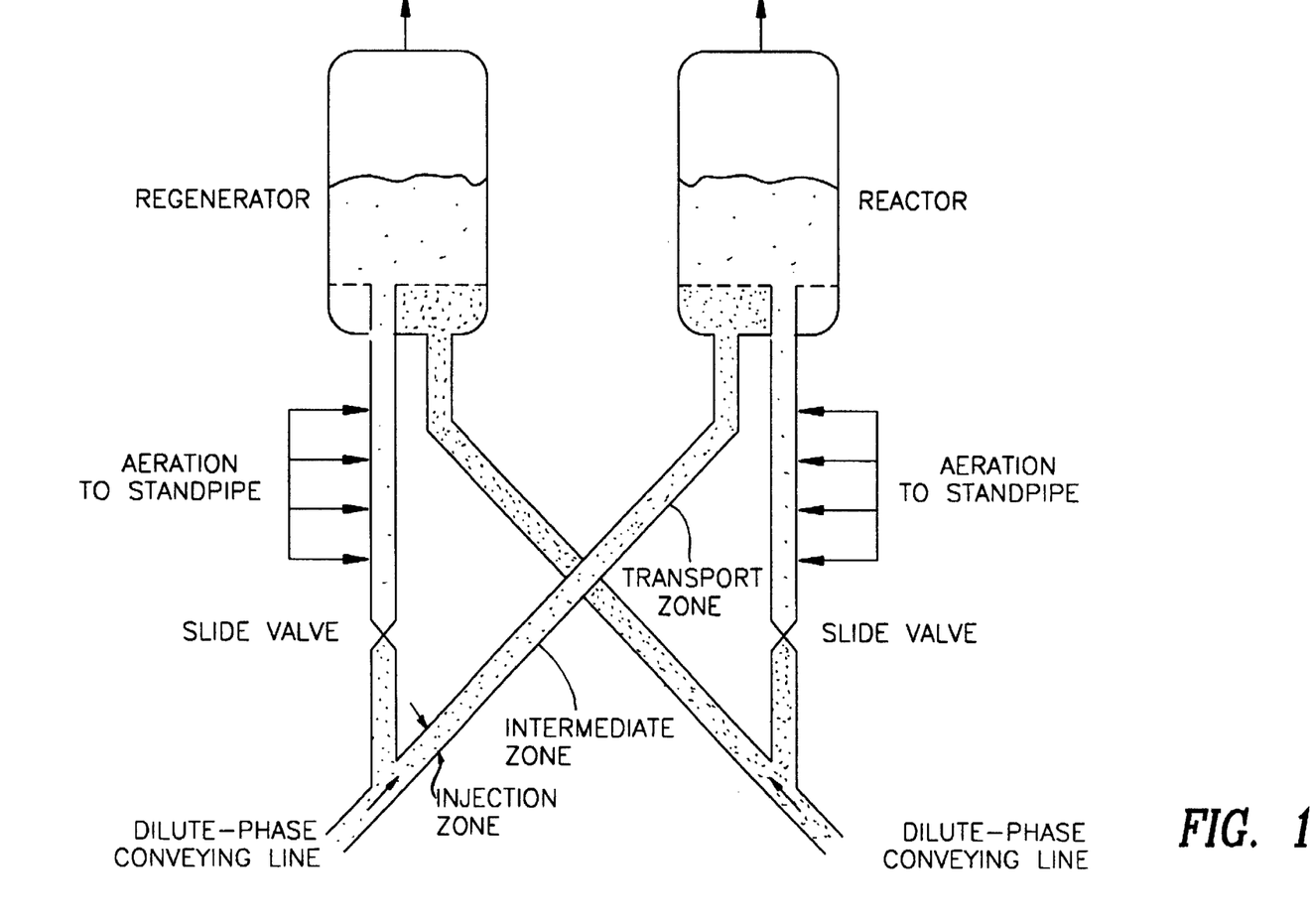
FIG. 1 is an example of transfer lines that convey catalyst particles in a fluid bed catalytic cracking process.

The present invention is a passive acoustic process to measure and monitor particle flow in a transfer line in which a gas/particle mixture is flowing. An example of such transfer lines are shown in FIG. 1 which schematically describes a catalytic cracker of oil to gasoline. The process is intended to assist operators of fluid bed reactors and combustion units in:

(1) optimizing the performance of their system with respect to mass transfer;
(2) identifying regions of the transfer line which depart from design with respect to mass transfer;
(3) identifying regions of the transfer line which are prone to wall erosion due to high particle velocities due either to component failure or changes in operating conditions. As noted high particle velocities also lead to particle attrition and excessive loss of catalyst particles as well as excessive generation of fines;
(4) identifying operating fluctuating operating states of the line that lead to transfer of "slugs" of particles which will eventually lead to structural or equipment failure.

Figure 2:
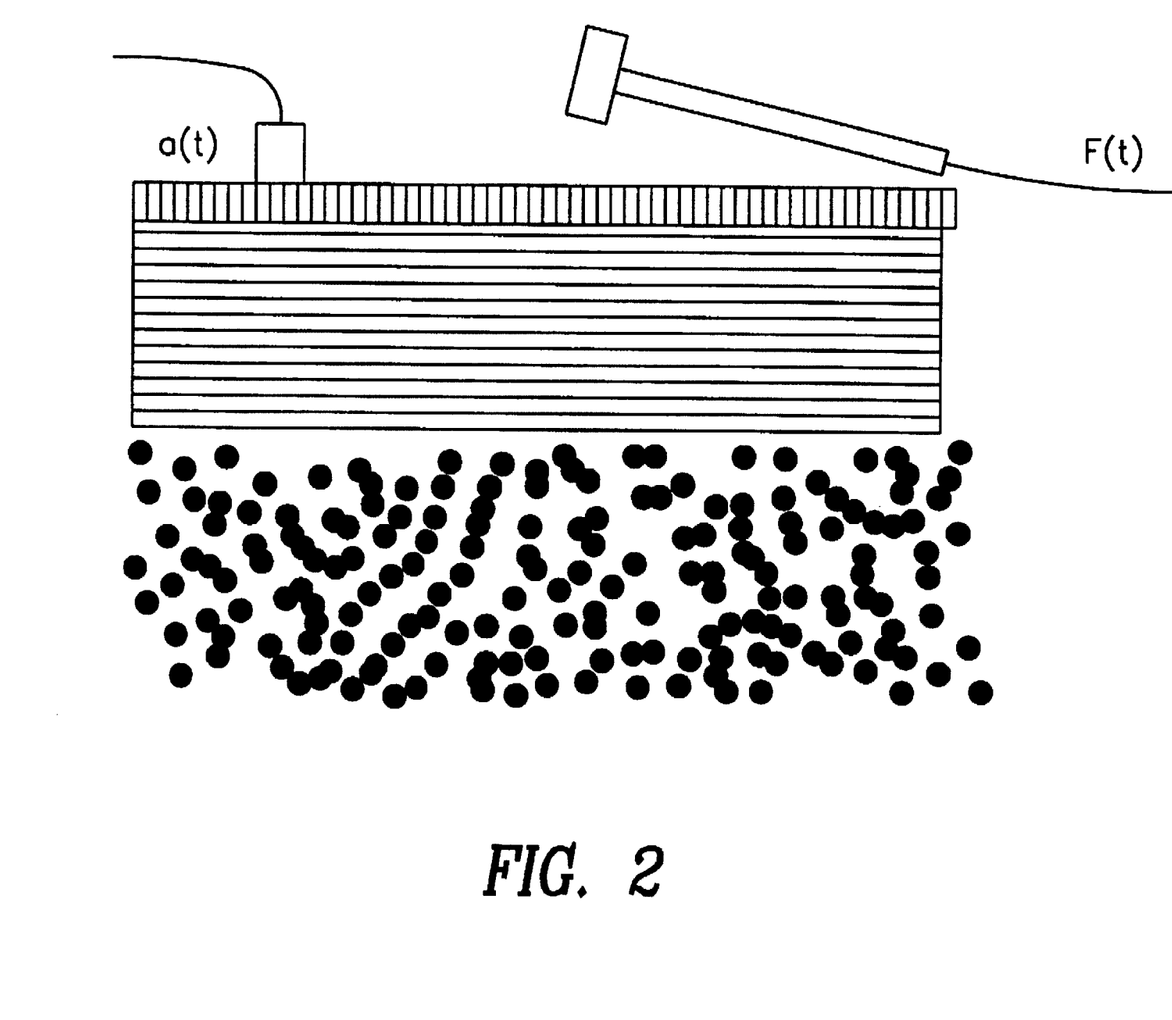
FIG. 2 shows a schematic of the measurement set up for monitoring of the wall vibrations of the composite wall of a transfer line produced by particle impact and also illustrating calibration of the response of the wall with an impact hammer.

In order to utilize the invention, accelerometers (for example, a Bruel and Kjaer 4384) are attached to the wall of the transfer line where it is desired to measure the flow characteristics as shown in FIG. 2. Attachment can be made either by a stud mounting for permanent installation or through a magnetic mount (for example, Bruel and Kjaer Type UA 0642) and a well polished surface for temporary mounting. If desired, the response of the accelerometer to particle impact can be calibrated by hitting the wall with an impact hammer (for example, a Bruel and Kjaer 8202) at the location in question.

Figure 3:
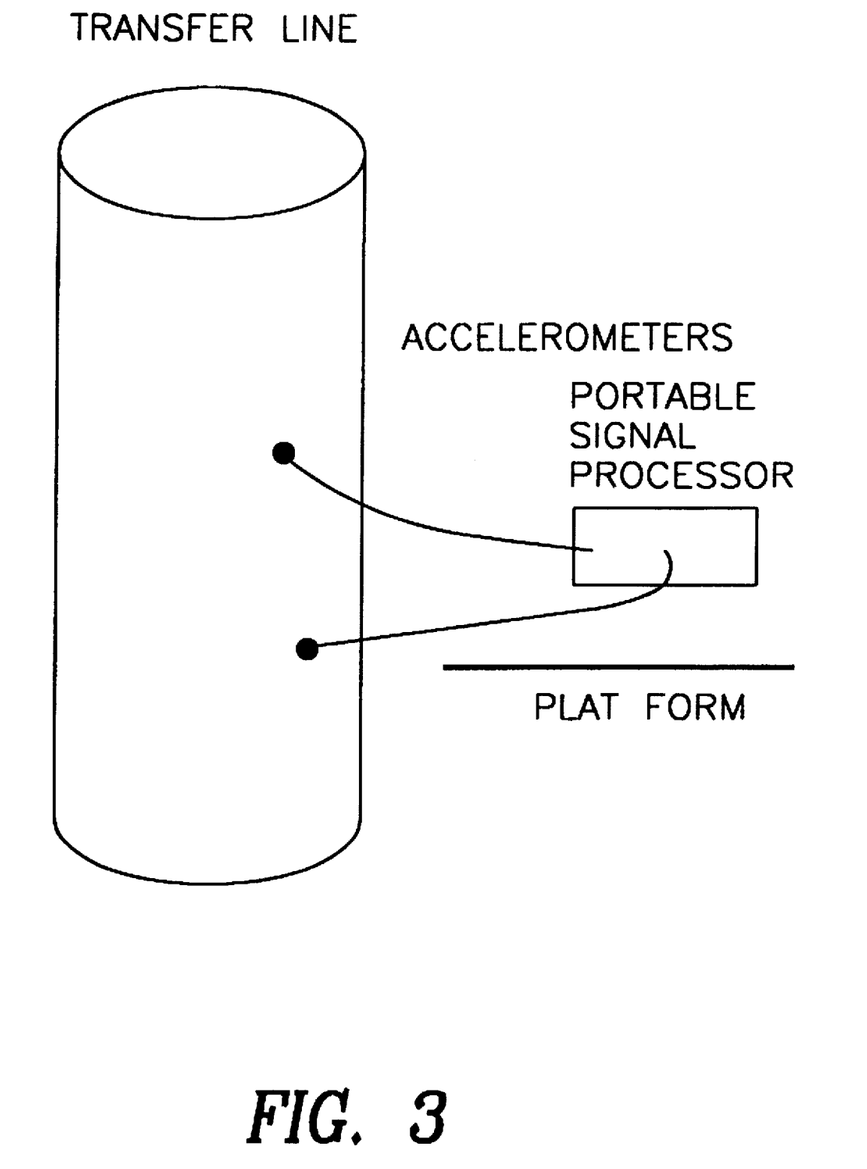
FIG. 3 shows a schematic of the monitoring set up to measure RMS acceleration for a portable system.

FIG. 3 indicates the process where the electrical signal from one or more accelerometers is converted to a voltage by a charge amplifier (for example a Bruel and Kjaer 2635) whose output is converted on the unit by a portable signal processor to the RMS acceleration over a band of frequencies that is dominated by particle impact noise. The output of the portable signal processor is stored for subsequent analysis.

Figure 4:
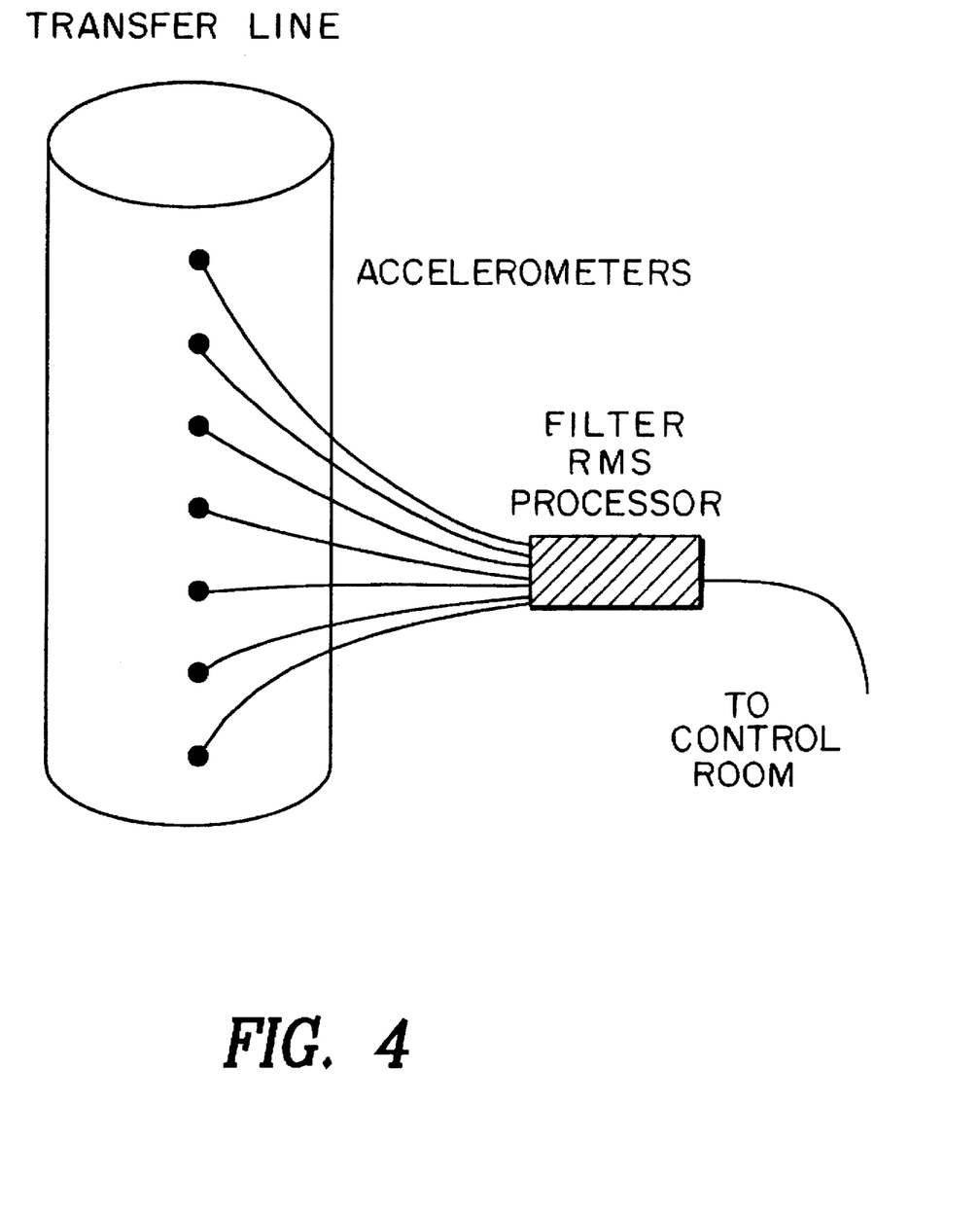
FIG. 4 shows a schematic of the monitoring set up to measure RMS acceleration for an on-line system.

FIG. 4 indicates another embodiment where the output of the accelerometer is again converted to a voltager by a charge amplifier (for example a Bruel and Kjaer 2635) but where a permanent digital system processes the data to produce a voltage proportional to the RMS acceleration over a band of frequencies that is dominated by particle impact noise. The output of acceleration over a band of frequencies that is dominated by particle impact noise. The output of the permanent digital system is then transmitted by suitable means to the control room where suitable algorithms convert it into a visual display of average particle velocity, average particle density, and average flux over the length of the transfer line. In the control room display significant departures from design are appropriately indicated.

Figure 5:
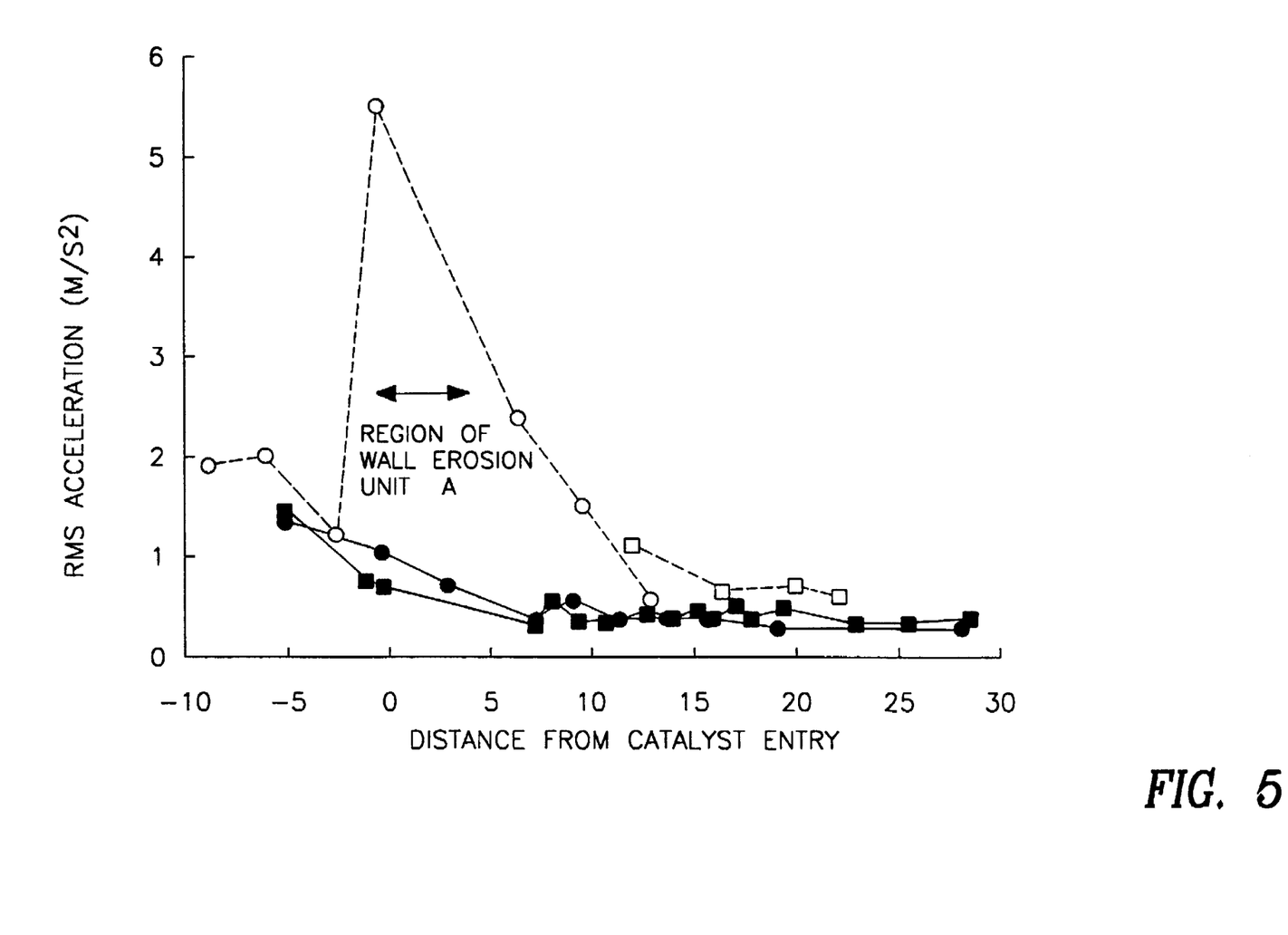
FIG. 5 shows an example of RMS Acceleration on transfer line measurements on transfer line on two identical units where one exhibits transfer line erosion and the other does not.

FIG. 5 is an example of the process that is the subject of this invention. Three curves are shown which plot RMS acceleration as a function of location on a transfer line. The curves indicated by the solid lines correspond to normal operation of the transfer line at two different times. The dashed curve corresponds to anomalous operation at two different times of the transfer line which lead to wall erosion of changes in operating conditions that lead to excessive particle velocities and hence wall erosion.

Figure 6:
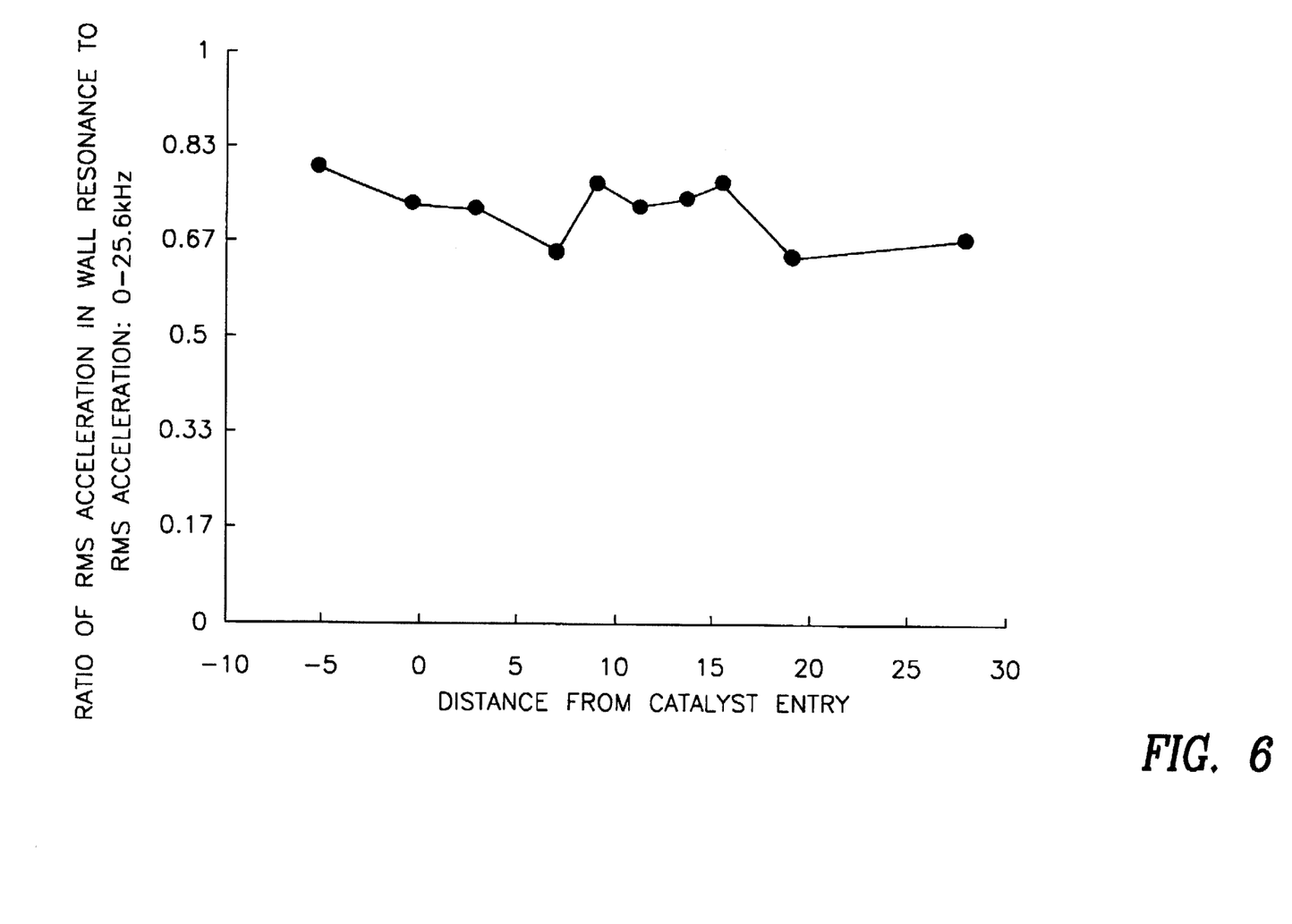
FIG. 6 shows independence of RMS acceleration on bandwidth.

The choice of the frequency band over which the RMS acceleration is defined is not critical as shown in FIG. 6, which is a plot of the ratio of the RMS Acceleration over a localized wall resonance (4 to 6 kHz) to the RMS acceleration over a band of 0 to 25.6 kHz.

Figure 7:
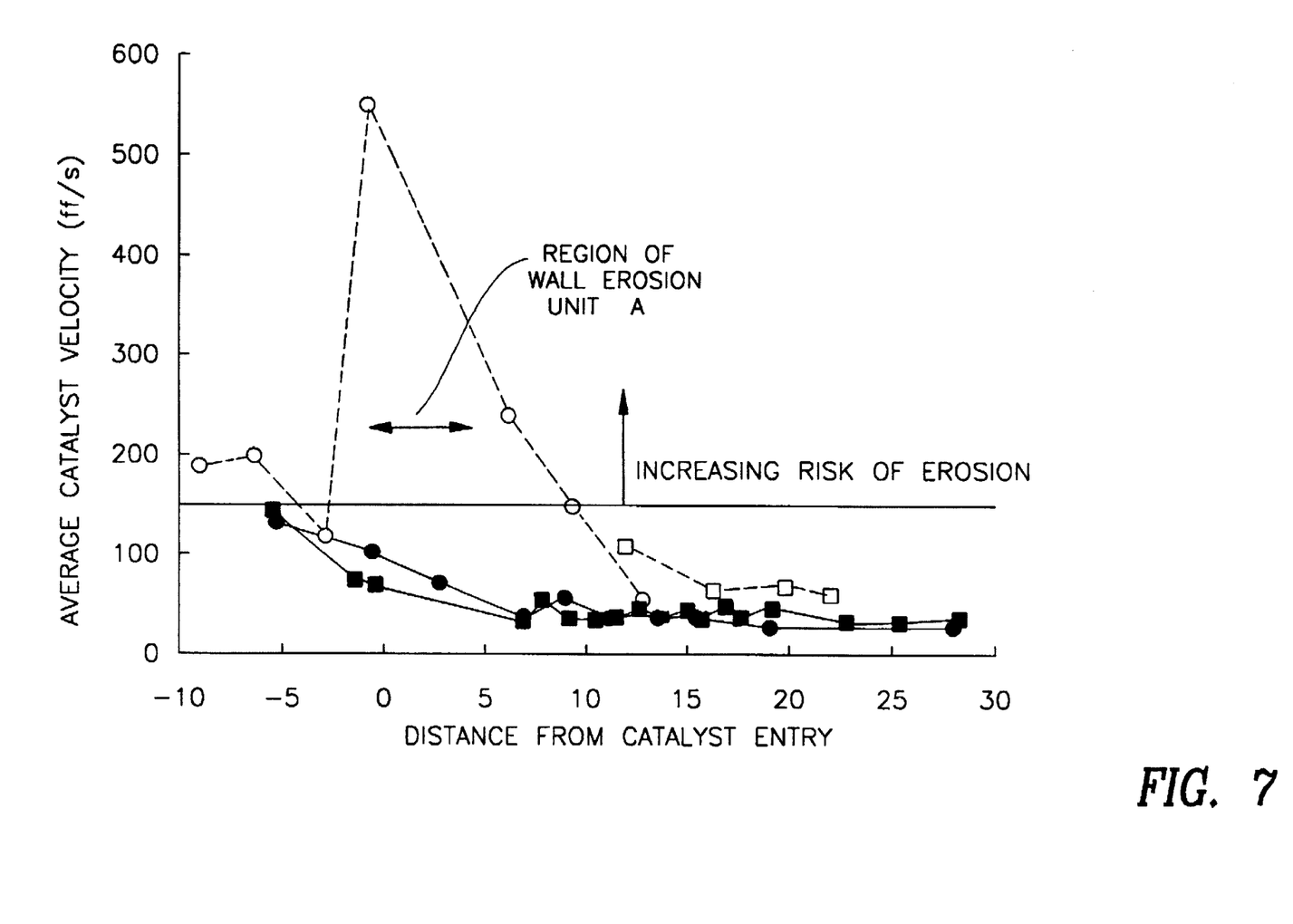
FIG. 7 shows a plot of estimated particle velocity at two different reactors.

FIG. 7 illustrates the conversion of RMS acceleration to particle velocity knowing the inner diameter of the transfer line and the mass flow rate in the line as described in Equation (17a). Erosion velocities for 100μ particles depend on the nature of the refractory but are usually considered to be above 200 ft/s. As noted high particle velocities also lead to particle erosion and excessive loss of catalysts as well as excessive generation of fines. The curves indicated by the solid lines correspond to normal operation of the transfer line at two different times. The dashed curve corresponds to anomalous operation at two different times of the transfer line which lead to wall erosion of changes in operating conditions that lead to excessive particle velocities and hence wall erosion.

Figure 8:
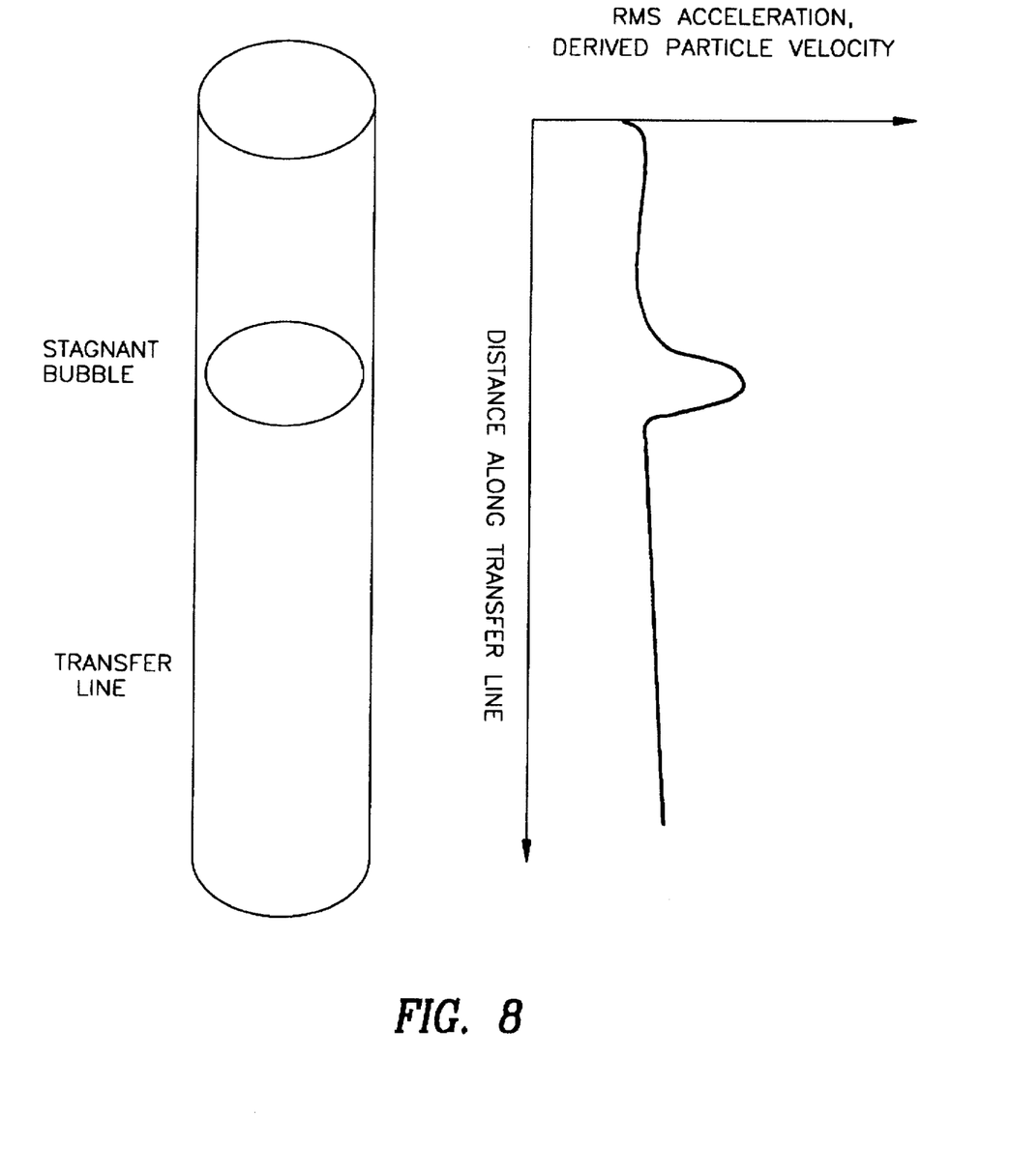
FIG. 8 shows a schematic plot of effect of stagnant bubbles on RMS accleration, A.

Occasionally it is possible to determine an empirical relationship between average particle velocity and average particle density in a transfer line. When this relationship exists, changes in RMS wall acceleration correspond to changes in particle flux. FIG. 8 is an illustration of how this phenomena can be applied to warn control room operators of the existence of slugging, or perhaps to display the change in flux as a function of time along with the time between slugs.

Figure 9:
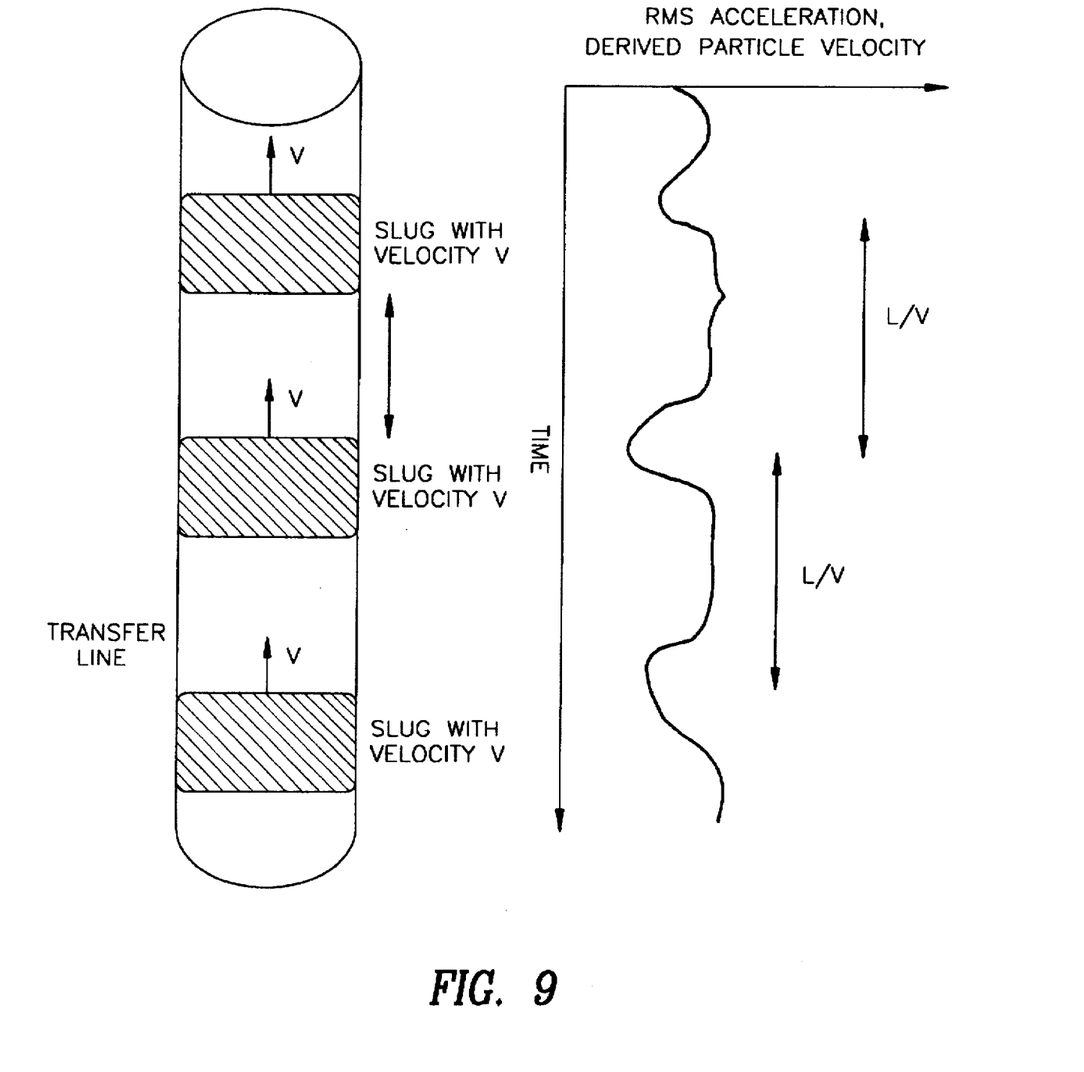
FIG. 9 shows a schematic plot of effect of slugging on the time variation of average particle velocity, $V_a$ and RMS Acceleration, A.

FIG. 9 exhibits the output of a portable system for both acceleration and velocity as a function of distance where the location of a stagnant bubble in the transfer line is exhibited.

Some flow malfunctions in transfer lines including symptoms and remedies are given in Table 1.

TABLE 1

| | SOME FLOW MALFUNCTIONS IN TRANSFER LINE: SYMPTOMS AND REMEDIES | | | |
|---|---|---|---|---|
| Parameters [Units] Conditions | $F = <V_p\rho_m>_s$ $F \sim V_a\rho_a$ [kg/m²s] | $V_a < V_p >_s$ [m/s] | $\rho_a = <\rho_m>_s$ [kg/m³] | Potential Operator Remedy |
| Normal | Design Value | Design Value | Design Value | None Needed Normal Operations |
| Wall Erosion or Particle Attrition | Uniform in Time | Local High at Erosion Attrition Point | Local Low at Erosion Attrition Point | Repair/Redesign/Change Operating State to Reduce $V_a$ |
| Stagnant Bubble | Uniform | Local High at Bubble | Local Low at Bubble | Repair/Redesign/Change Operating State to Eliminate Bubble |
| Slugging | Pulsing in Time | Pulsing in Time | Pulsing in Time | Repair/Redesign/Change Operating State |

EXAMPLE

One use of this invention is to monitor the transfer lines/injectors of a fluidized bed coal combustion unit.

Fluidized bed combustion of coal is an alternative to the traditional combustion methods that rely on pulverized coal. Fluidized bed coal combustion is advantageous because boilers using this technology emit fewer pollutants, have higher heat transfer coefficients, and operate at lower temperatures that pulverized coal units. Because of these advantages, the use of fluidized bed coal combustion has increased dramatically in recent years.

Figure 10:
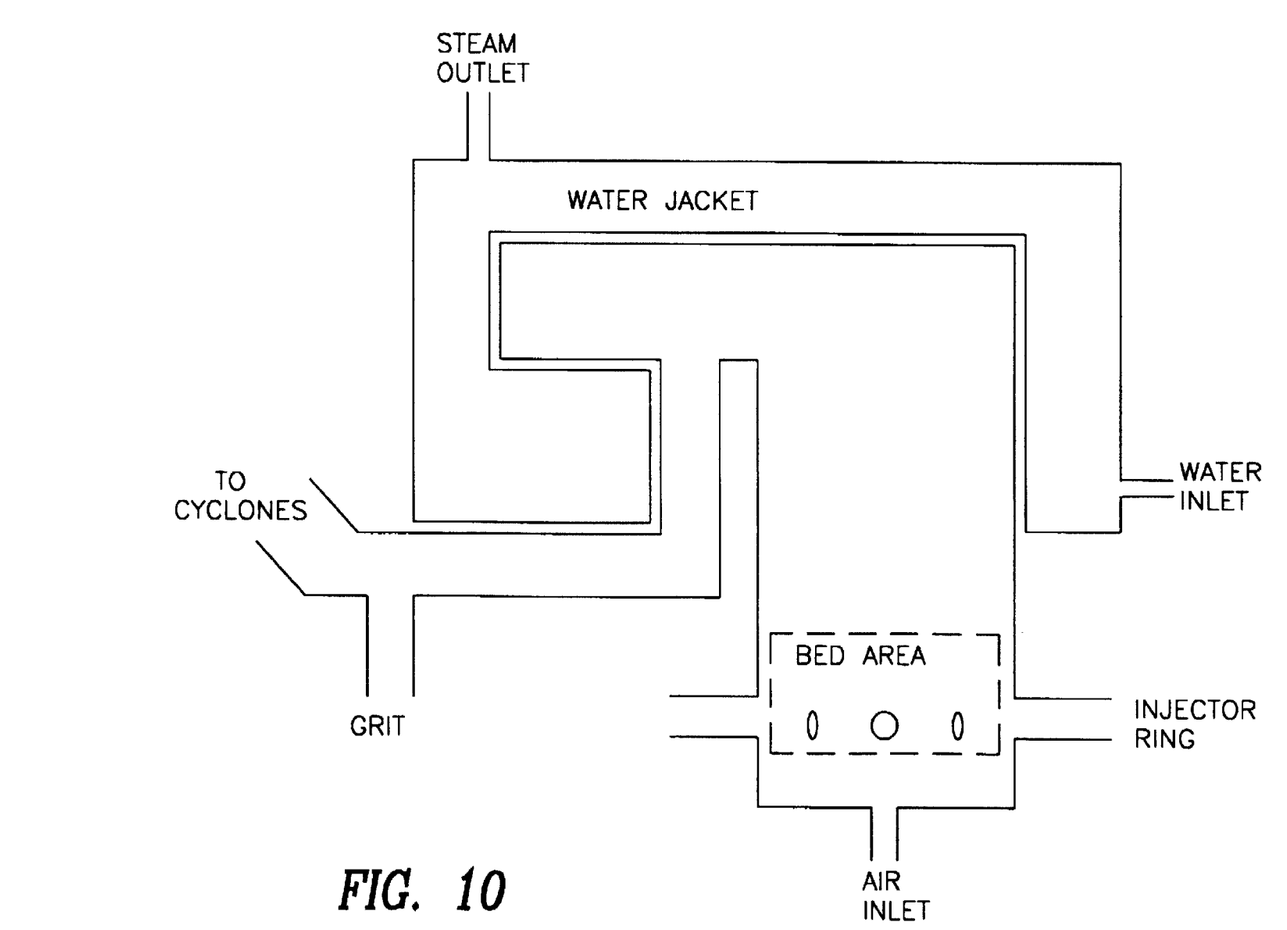
FIG. 10 is a schematic representation of a fluidized bed coal combuster.
Figure 11:
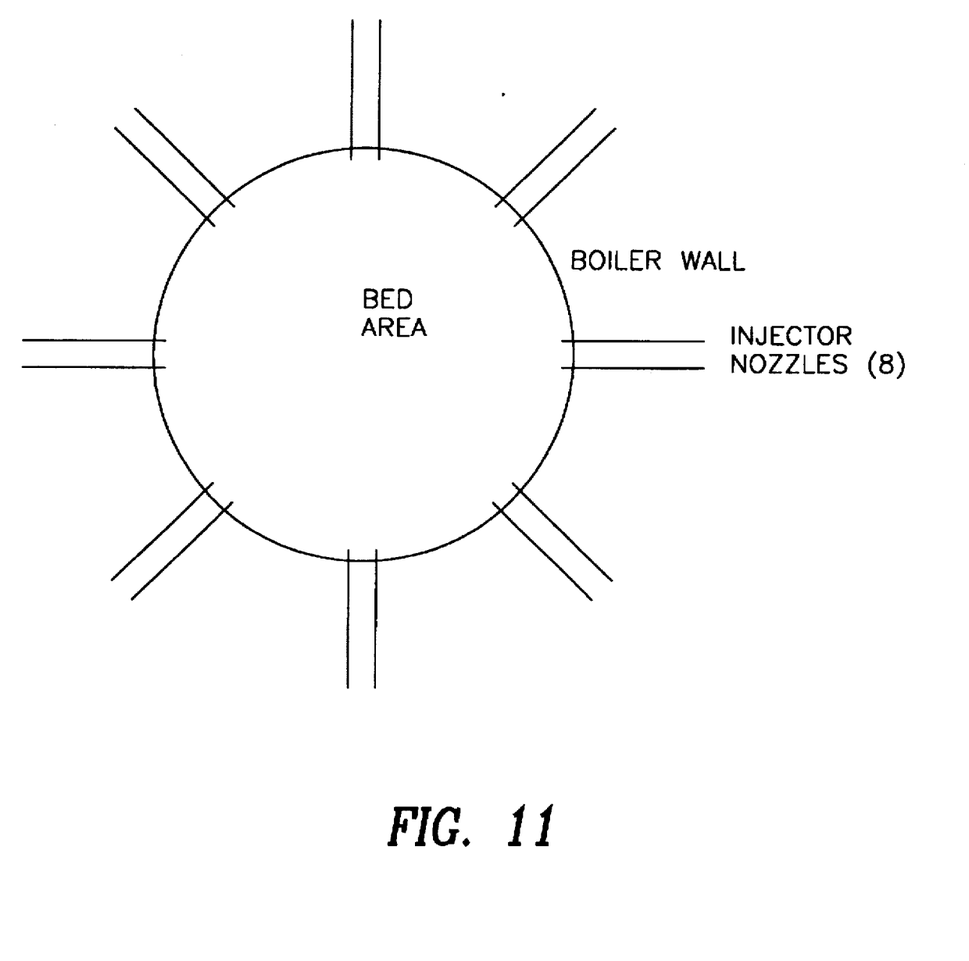
FIG. 11 shows the circumferential arrangement of coal injectors around the bed of a fluidized bed coal combuster.

A fluidized bed coal combuster is shown schematically in FIG. 10. One challenge facing the operator of a fluidized bed coal combuster is properly feeding coal into the bed. Coal must be introduced so that it is evenly distributed over the entire bed area. Coal rich zones that result from uneven distributions are detrimental to the operation of the unit. One method of overcoming this difficulty is to introduce the coal through a number of coal injectors arranged circumferentially around the bed, as shown in FIG. 11.

This invention can be used to monitor the performance of each nozzle, and to provide real time displays of the wall accelerations, the mass flux of coal, the average particle density, and the average particle velocity within the transfer lines that lead to the injector nozzles. To make these measurements, accelerometers are physically attached to the transfer lines by one of the method described above. An initial test must be conducted to ensure that the accelerometers are properly placed. The flux in the transfer line is then measured and compared to the changes in the signal from the accelerometer that occur in the same time period. A correlation between mass flux and wall acceleration indicates that the accelerometers are properly placed.

Once the accelerometers have been properly placed, the invention can be used to monitor the transfer lines that lead to the injectors. Any change in RMS wall acceleration with respect to the other lines is an indication of a change in either flux or velocity. Therefore, a one time calibration that equalizes the RMS wall acceleration of each line at a particular point along the lines, or an independent calibration, allows one to measure changes in either flux or velocity. The values of either flux or velocity are then displayed to the unit operator who can take the appropriate steps to optimize the operation of the combuster.

What is claimed is:

1. A method for the non intrusive determination of average particle velocity, average particle mass density, and average mass flux in a gas/particle transfer line as a function of either position along the line or elapsed time comprising:

(a) measuring wall vibrations of said transfer line at more than one position along a length of said transfer line at a particular time as gas and particles move along the length of said transfer line to determine a power spectrum of said wall vibrations, (b) determining the RMS acceleration from said power spectrum, (c) determining the average mass flux through said transfer line, and (d) determining the average particle mass density and the average particle velocity from said RMS acceleration and said average mass flux at a particular time and position along said transfer line.

2. The method of claim 1 further comprising the step of determining at least one of said average particle mass density and said average particle velocity from said RMS acceleration and said average mass flux at a later time.

3. The method of claim 2 further comprising the step of determining the change in said at least one of said average particle mass density and said average particle velocity as a function of position along said transfer line.

4. The method of claim 1 wherein said average particle velocity is proportional to the RMS acceleration and inversely proportional to the square-root of the average mass flux.

5. The method of claim 1 wherein said average particle mass density is proportional to the three-halves power of the average mass flux and inversely proportional to the RMS acceleration.

6. The method of claim 1 further comprising the step of determining at least one of said average particle mass density and said average particle velocity from said RMS acceleration and said average mass flux at a different position along the transfer line.

7. The method of claim 2 further comprising the step of determining the change in said at least one of said average particle mass density and said average particle velocity as a function of time.

* * * * *